US010642256B2

(12) United States Patent
Rocci et al.

(10) Patent No.: US 10,642,256 B2
(45) Date of Patent: May 5, 2020

(54) METHOD AND APPARATUS FOR UNIFIED PERSONAL CLIMATE MANAGEMENT

(71) Applicant: FORD GLOBAL TECHNOLOGIES, LLC, Dearborn, MI (US)

(72) Inventors: Benjamin M. Rocci, Plymouth, MI (US); Michael David Beeney, Canton, MI (US); Mark Anthony Rockwell, Wyandotte, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 354 days.

(21) Appl. No.: 15/613,680

(22) Filed: Jun. 5, 2017

(65) Prior Publication Data
US 2018/0348740 A1    Dec. 6, 2018

(51) Int. Cl.
*G05B 19/418* (2006.01)
*G06K 9/00* (2006.01)
*G06K 9/62* (2006.01)
*G16B 99/00* (2019.01)

(52) U.S. Cl.
CPC ....... *G05B 19/418* (2013.01); *G06K 9/00845* (2013.01); *G06K 9/00892* (2013.01); *G06K 9/6289* (2013.01); *G16B 99/00* (2019.02)

(58) Field of Classification Search
CPC .. G05B 19/418; G16B 99/00; G06K 9/00892; G06K 9/6289
See application file for complete search history.

(56) References Cited

U.S. PATENT DOCUMENTS

| | | | |
|---|---|---|---|
| 9,919,712 B1* | 3/2018 | Doyen | B60W 40/08 |
| 10,291,624 B1* | 5/2019 | Cronin | H04L 63/102 |
| 2014/0309789 A1 | 10/2014 | Ricci | |
| 2015/0057875 A1* | 2/2015 | McGinnis | G05B 19/418 |
| | | | 701/31.6 |
| 2015/0363986 A1* | 12/2015 | Hoyos | H05K 999/99 |
| | | | 340/5.61 |
| 2016/0042627 A1* | 2/2016 | Foley | B60Q 9/00 |
| | | | 340/576 |
| 2016/0167479 A1* | 6/2016 | Morin | B60Q 1/50 |
| | | | 701/48 |
| 2016/0193895 A1 | 7/2016 | Aich et al. | |
| 2017/0247000 A1* | 8/2017 | Ricci | G06K 9/00302 |
| 2017/0253201 A1* | 9/2017 | Maeshiro | B60S 1/023 |
| 2017/0330044 A1* | 11/2017 | Telpaz | B60H 1/00742 |
| 2018/0201092 A1* | 7/2018 | Ahuja | B60H 1/00771 |
| 2018/0247067 A1* | 8/2018 | Hrabak | G06F 21/6218 |
| 2018/0321700 A1* | 11/2018 | Kwak | F24F 11/50 |
| 2019/0061772 A1* | 2/2019 | Prinz | A61B 5/18 |

* cited by examiner

*Primary Examiner* — Hee K Song
(74) *Attorney, Agent, or Firm* — Mike Spenner; Brooks Kushman P.C.

(57) ABSTRACT

A system includes a processor configured to determine that a first user will transition from a first climate-controllable environment to a second climate-controllable environment within a threshold time. The processor is also configured to compare first and second environment temperatures. The processor is further configured to detect whether a second-user control device is in communication with a second-environment climate control and set the second-environment climate control to a desired temperature, based on the first environment temperature, responsive to an absence of the second-user control device.

19 Claims, 6 Drawing Sheets

METHOD AND APPARATUS FOR UNIFIED PERSONAL CLIMATE MANAGEMENT

TECHNICAL FIELD

The illustrative embodiments generally relate to methods and apparatuses for unified personal climate management.

BACKGROUND

Devices are becoming more and more "intelligent" every year. Thermostats, music players, door controls and various other home aspects are swiftly being automated. Software integrated and functioning in conjunction with these devices can give an illusion of intelligence. The devices can react to personal user state experiences, and they can provide a dynamic and adaptive experience that makes it appear as though the device is responding to a detected user condition.

One of the earliest "smart" home devices was the thermostat. Companies such as HONEYWELL and NEST produced thermostats that were adaptive and could function in concert with other devices, to control temperature in a house in a more refined manner than ever before. While this represented a marked improvement over older thermostats, the user still had to set a schedule and a series of parameters that the control system adhered to. As devices become more adaptive and capable of greater processing and communication, there is an opportunity to improve the apparent "intelligence" of the devices to make them appear to be even more autonomous.

SUMMARY

In a first illustrative embodiment, a system includes a processor configured to receive a user biometric measurement from a wirelessly connected device. The processor is also configured to determine a climate adjustment responsive to a comparison of the biometric measurement to a stored baseline value or range and activate a vehicle climate control to reflect the climate adjustment.

In a second illustrative embodiment, a system includes a processor configured to determine that a first user will transition from a first climate-controllable environment to a second climate-controllable environment within a threshold time. The processor is also configured to compare first and second environment temperatures. The processor is further configured to detect whether a second-user control device is in communication with a second-environment climate control and set the second-environment climate control to a desired temperature, based on the first environment temperature, responsive to an absence of the second-user control device.

In a third illustrative embodiment, a system includes a processor configured to detect a user-initiated change to a current environment control. The processor is also configured to determine if another environmental control is pre-definedly associated with a user enacting the user-initiated change. The processor is further configured to determine when a user will likely transition to another environment controlled by the another environmental control and instruct the another environmental control to adjust a temperature to reflect the user-initiated change, at a time within a predetermined threshold before the user will likely transition.

DETAILED DESCRIPTION

As required, detailed embodiments are disclosed herein; however, it is to be understood that the disclosed embodiments are merely illustrative and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the claimed subject matter.

Figure 1:
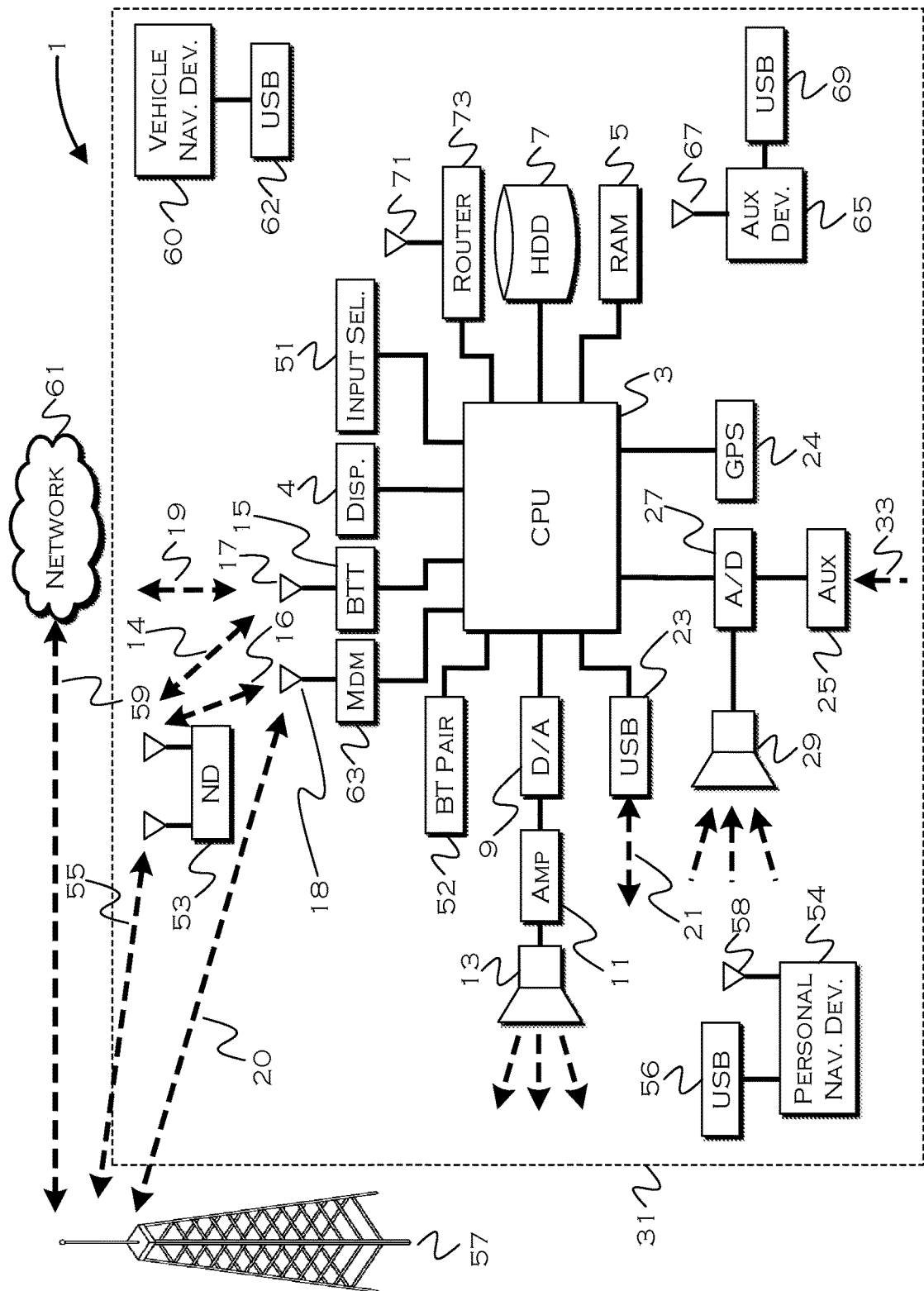
FIG. 1 shows an illustrative vehicle computing system.

FIG. 1 illustrates an example block topology for a vehicle-based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, spoken dialog system with automatic speech recognition and speech synthesis.

In the illustrative embodiment 1 shown in FIG. 1, a processor 3 controls at least some portion of the operation of the vehicle-based computing system. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory. In general, persistent (non-transitory) memory can include all forms of memory that maintain data when a computer or other device is powered down. These include, but are not limited to, HDDs, CDs, DVDs, magnetic tapes, solid state drives, portable USB drives and any other suitable form of persistent memory.

The processor is also provided with a number of different inputs allowing the user to interface with the processor. In this illustrative embodiment, a microphone 29, an auxiliary input 25 (for input 33), a USB input 23, a GPS input 24, screen 4, which may be a touchscreen display, and a BLUETOOTH input 15 are all provided. An input selector 51 is also provided, to allow a user to swap between various inputs. Input to both the microphone and the auxiliary connector is converted from analog to digital by a converter 27 before being passed to the processor. Although not shown, numerous of the vehicle components and auxiliary components in communication with the VCS may use a vehicle network (such as, but not limited to, a CAN bus) to pass data to and from the VCS (or components thereof).

Outputs to the system can include, but are not limited to, a visual display 4 and a speaker 13 or stereo system output. The speaker is connected to an amplifier 11 and receives its signal from the processor 3 through a digital-to-analog converter 9. Output can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., cell phone, smart phone, PDA, or any other device having wireless remote network connectivity). The nomadic device can then be used to communicate 59 with a network 61 outside the vehicle 31 through, for example, communication 55 with a cellular tower 57. In some embodiments, tower 57 may be a Wi-Fi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device). Bluetooth is a subset of the IEEE 802 PAN (personal area network) protocols. IEEE 802 LAN (local area network) protocols include Wi-Fi and have considerable cross-functionality with IEEE 802 PAN. Both are suitable for wireless communication within a vehicle. Another communication means that can be used in this realm is free-space optical communication (such as IrDA) and non-standardized consumer IR protocols.

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example). While frequency division multiplexing may be common for analog cellular communication between the vehicle and the internet, and is still used, it has been largely replaced by hybrids of Code Domain Multiple Access (CDMA), Time Domain Multiple Access (TDMA), Space-Domain Multiple Access (SDMA) for digital cellular communication. If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., Wi-Fi) or a WiMax network.

In one embodiment, incoming data can be passed through the nomadic device via a data-over-voice or data-plan, through the onboard BLUETOOTH transceiver and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58, a vehicle navigation device 60 having a USB 62 or other connection, an onboard GPS device 24, or remote navigation system (not shown) having connectivity to network 61. USB is one of a class of serial networking protocols. IEEE 1394 (FireWire™ (Apple), i.LINK™ (Sony), and Lynx™ (Texas Instruments)), EIA (Electronics Industry Association) serial protocols, IEEE 1284 (Centronics Port), S/PDIF (Sony/Philips Digital Interconnect Format) and USB-IF (USB Implementers Forum) form the backbone of the device-device serial standards. Most of the protocols can be implemented for either electrical or optical communication.

Further, the CPU could be in communication with a variety of other auxiliary devices 65. These devices can be connected through a wireless 67 or wired 69 connection. Auxiliary device 65 may include, but are not limited to, personal media players, wireless health devices, portable computers, and the like.

Also, or alternatively, the CPU could be connected to a vehicle based wireless router 73, using for example a Wi-Fi (IEEE 803.11) 71 transceiver. This could allow the CPU to connect to remote networks in range of the local router 73.

In addition to having exemplary processes executed by a vehicle computing system located in a vehicle, in certain embodiments, the exemplary processes may be executed by a computing system in communication with a vehicle computing system. Such a system may include, but is not limited to, a wireless device (e.g., and without limitation, a mobile phone) or a remote computing system (e.g., and without limitation, a server) connected through the wireless device. Collectively, such systems may be referred to as vehicle associated computing systems (VACS). In certain embodiments particular components of the VACS may perform particular portions of a process depending on the particular implementation of the system. By way of example and not limitation, if a process has a step of sending or receiving information with a paired wireless device, then it is likely that the wireless device is not performing that portion of the process, since the wireless device would not "send and receive" information with itself. One of ordinary skill in the art will understand when it is inappropriate to apply a particular computing system to a given solution.

In each of the illustrative embodiments discussed herein, an exemplary, non-limiting example of a process performable by a computing system is shown. With respect to each process, it is possible for the computing system executing the process to become, for the limited purpose of executing the process, configured as a special purpose processor to perform the process. All processes need not be performed in their entirety, and are understood to be examples of types of processes that may be performed to achieve elements of the invention. Additional steps may be added or removed from the exemplary processes as desired.

With respect to the illustrative embodiments described in the figures showing illustrative process flows, it is noted that a general purpose processor may be temporarily enabled as a special purpose processor for the purpose of executing some or all of the exemplary methods shown by these figures. When executing code providing instructions to perform some or all steps of the method, the processor may be temporarily repurposed as a special purpose processor, until such time as the method is completed. In another example, to the extent appropriate, firmware acting in accordance with a preconfigured processor may cause the processor to act as a special purpose processor provided for the purpose of performing the method or some reasonable variation thereof.

Figure 2:
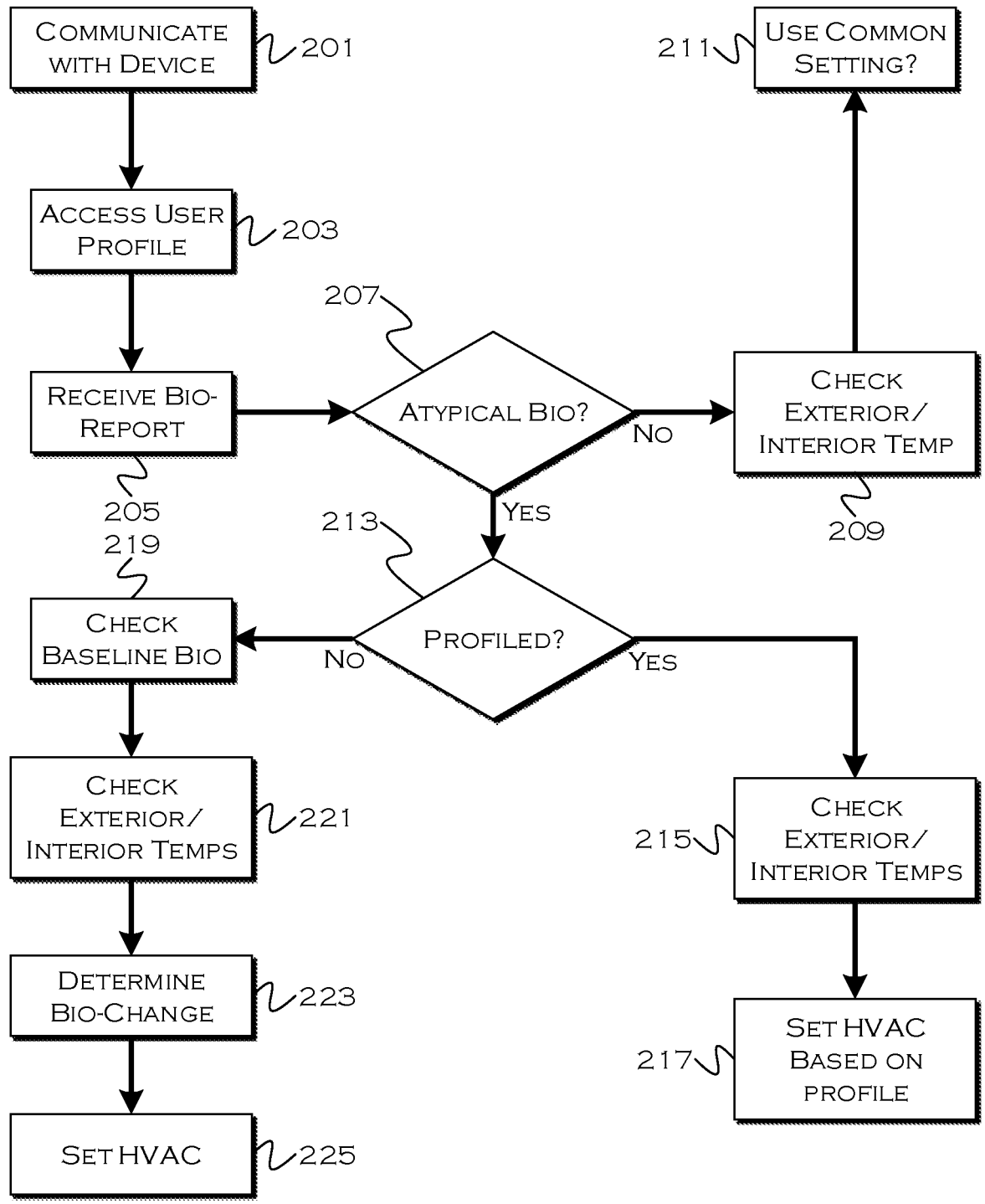
FIG. 2 shows an illustrative example of a climate control process related to user biometrics.

FIG. 2 shows an illustrative example of a climate control process related to user biometrics. In this illustrative example, the process controls climate based on a detected change to a user biometric state. This could include, for example, lowering climate temperature following a run, raising climate temperature following sledding, etc.

In this example, the process communicates 201 with a user device (e.g., a smart-watch) that includes at least one biometric sensor. The biometric sensor could vary in type, and could include, but is not limited to, heart-rate sensors, skin temperature sensors, etc.

The process also accesses 203 a user profile, stored, for example, locally on a vehicle (where the process may be executed), on a smart device (the user device or another user device, such as a phone), on the cloud, etc. The user profile includes baseline biometric data, previously recorded by the same or a similar biosensor, and user temperature preferences. The temperature preferences may also be stored with respect to various baseline and anomalous biometric conditions (e.g., if heart-rate is baseline, the user prefers temperature of 72 degrees Fahrenheit, if heart-rate is more than 20% above baseline, the user prefers temperature of 68 degrees Fahrenheit). This data about the user's preferred temperatures under certain biometric conditions can assist the process in determining an appropriate climate setting.

The process also receives 205 a bio-report, reporting at least one user biometric condition, from the connected device. In the examples, heart-rate will be used primarily as the example, as it is likely the most common biometric measured by wearable devices, but other bio-characteristics can also be used in a logical manner as the basis for temperature control.

If the biometric (heart-rate, in this example) reading is atypical 207 based on the user profile (or based on an expected baseline, if no user profile exists), the process engages in strategic temperature setting. If the biometric is within a predefined threshold of the expected baseline biometric reading, the process will engage in a "standard" climate setting process according to the illustrative embodiments. This portion of the process involves determining the present interior (of the vehicle) and exterior temperatures 209 and engaging 211 a user-preferred setting that dictates what interior temperature the user prefers based on the detected exterior temperature.

If the biometric is atypical, the process determines if a user profile exists that includes data corresponding to the measured biometric 213. If the user and biometric profile exist, the process may again check 215 the interior and exterior temperatures and use 217 the user profile to set an preferred HVAC setting for the vehicle.

For example, if a user device measures skin temperature and heart-rate, the device may read a skin temperature of 80 degrees Fahrenheit and a heart-rate of 125 bpm. Since the skin temperature is outside the normal range of 90-95 degrees, and the heart-rate is elevated, the user has likely been doing some form of outdoor activity in cold weather. The process may have user preferred settings that indicate that the user typically prefers HVAC settings to cool the vehicle to 68 degrees when the user has a high heart-rate, but the skin temperature may serve as an indicator that the user is already cold. In this case, the user profile may already have settings for sledding or skiing (outdoor cold activities) which include lowered skin temperatures and raised heart-rates. If the settings exist for the detected conditions, the process controls the vehicle climate based on those settings to set the desired temperature.

If the settings do not exist for at least one biometric, the system can still use the data from that biometric to select an appropriate temperature. In the above example, the system may have a default setting of 90 degrees in the presence of lowered skin temperature (with the goal being to raise the skin temperature to a standard minimum), which can be used to temper the HVAC settings expected for a high heart-rate. If the HVAC was normally set at 68 degrees for a raised heart-rate, the process may elect a number somewhere between 90 and 68, based on, for example, a predefined ratio in a lookup table, designed to raise the user's exterior temperature while not making it too hot so as to be immediately uncomfortable, in light of the elevated heart-rate.

If the user does not have a profile, or if the user profile does not have biometric data defining settings preferred by that user for various biometric readings, the process may determine 219 a baseline biometric for the user (based on standard data or recorded biometric data, which may be present even in the absence of a corresponding temperature setting).

Based on a deviance between baseline biometric data and measured biometric data, and a reference 221 to vehicle interior and exterior temperatures, the process may determine 223 a desired bio-state change. The process may then set 225 the HVAC in accordance with the desired bio-state change.

Figure 3:
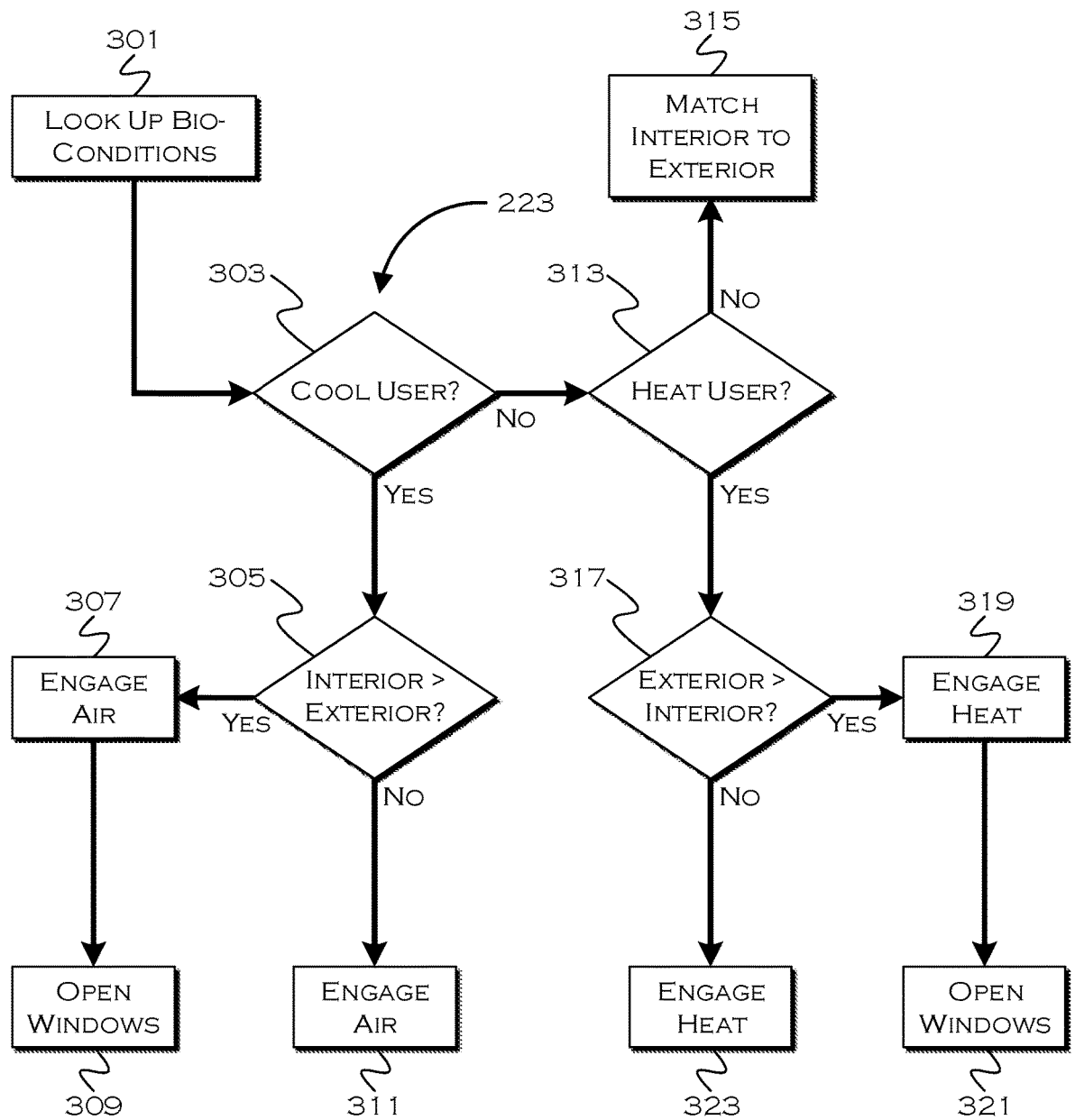
FIG. 3 shows an illustrative example of a setting selection process related to user biometrics.

FIG. 3 shows an illustrative example of a setting selection process related to user biometrics. This process represents a non-limiting example of the sort of process that can performed by the process described with respect to FIG. 2. In this example, the process examines or retrieves baseline or recommended biometric conditions for a user. For example, if a user heart-rate is elevated and/or user skin temperature is high, the process may determine 303 that it is appropriate under that combination of conditions to cool a user. On the other hand, as previously noted, high heart-rate and low skin temperature may be an indication to heat up a user, although perhaps not as hot as would be desired with normal heart-rate and low skin temperature. The exact determination made based on the combination of existing received biometric conditions can be based on preformulated combinations and/or observed user preferences under previous conditions. Since variables such as skin temperature and heart-rate tend to have a wide spectrum, the process may consider actions based on a value being within a predefined or observed categorical range (e.g., heart-rates between X and Y represent medium level activity for a given user).

If the process decides 303 that the user should be cooled off, the process may determine 305 if the vehicle interior temperature is greater than the exterior temperature. If this is the case, the process will engage air conditioning 307 in an attempt to lower the interior temperature in an effort to cool off an occupant. Also, in this example, the process may open 309 or partially open the windows, to allow cooler air from outside a vehicle to enter and cool the vehicle. As the temperature normalizes with that of the outside, or as the air conditioning accelerates in function, the process could close the windows to prevent cold air from escaping (the same can be said if windows are lowered in an effort to raise the temperature and the heat is engaged).

If the interior temperature is less than the exterior temperature, the process may still elect to engage 311 the air conditioning if the desired cabin temperature is not yet realized. In this case, it does not necessarily make sense to open the windows, as the outside air is hotter than the inside air. The degree and duration of HVAC engagement can depend on the deviation between a current and expected future temperature, and whether or not the desired temperature is reached (at which point the HVAC can be selectively disengaged).

A decision with respect to the timing of engaging the heating or cooling can be based on a variety of factors. In one example, the user may be approaching the vehicle and the vehicle may actually detect the user approach. In this case, the system may run at a maximum heating or cooling rate, since there is limited time before the user enters the vehicle, and any variation in temperature may be slight before entry. Once the user enters, the system may continue to operate at the maximum, until the desired temperature is achieved, or the process may slow the rate to a level to be maintained until the desired temperature is achieved. In other examples, the process may know or predict when a user will enter the vehicle, and the actual observed or known rate of heating or cooling, based on, for example, cabin size, current interior and current exterior temperature. That is, when it is −20 degrees Fahrenheit outside, and the desired interior temperature should be raised from −10 degrees to 72 degrees, it may take significant time and effort to heat the cabin. On the other hand, raising the interior temperature from 68 degrees to 72 degrees, when the exterior temperature is 70 degrees, may take a minimal amount of heating. Rates can be predicted or known based on past observations for a given vehicle.

In a similar manner, if the system elects 313 to heat a cold user, the process may determine 317 if the interior temperature is lower than the exterior temperature. If it is cooler inside the vehicle than outside, the process may engage the heat 319 and open the windows if appropriate (as previously discussed). Otherwise, the process may simply engage 323 the heat.

If there is no clear reason to heat or cool a user, that is, if the biometrics indicate the user is likely comfortable in a current temperature state, the process may attempt to match 315 interior and exterior temperatures, so that the vehicle temperature closely replicates the exterior temperature in which the user is currently comfortable. If the user is in an office or other climate, which can be known through a variety of determinations, the vehicle may match the temperature to the house or office, as opposed to the exterior temperature.

Figure 4:
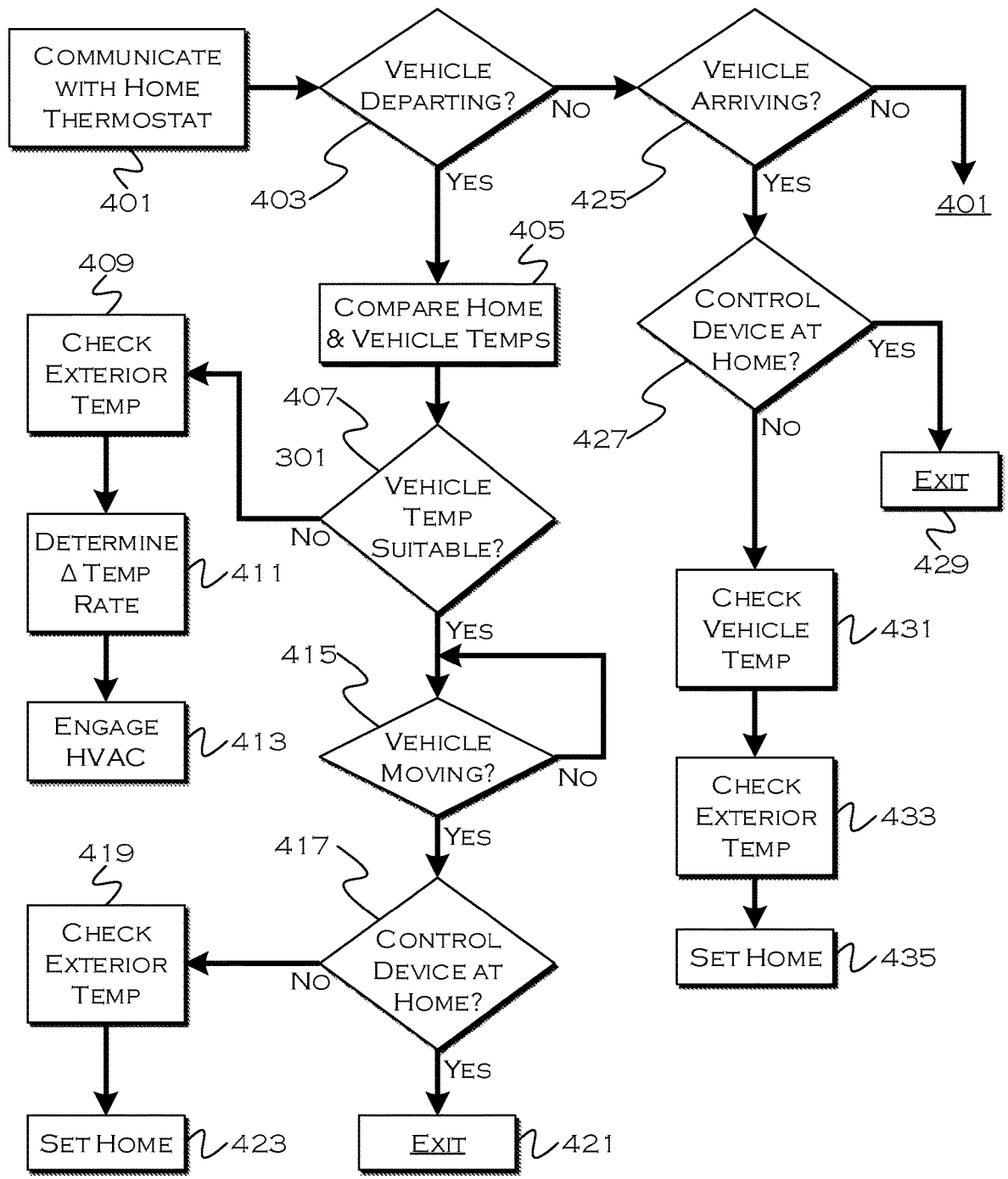
FIG. 4 shows an illustrative climate synchronization process.

FIG. 4 shows an illustrative climate synchronization process. In this example, the vehicle and a home thermostat or climate control system work to synchronize temperatures for maximum user comfort. In this example, the process executes on the cloud and establishes communication 401 between a vehicle and a home (or other local) thermostat or climate control system. In this example, the process can work to set an away or arriving temperature, so the process determines 403 if the vehicle is departing or determines 425 if the vehicle is arriving. If the vehicle is neither arriving or departing, the process may loop to 401 until the vehicle nears a known destination or likely destination.

If the vehicle is departing a location, the process works to establish an away-temperature for the location from which the user is departing, in addition to climatizing the vehicle to match a user preference. In incidents of extreme weather, a user may want a vehicle very hot or very cool upon entry (much hotter or cooler than a house), and then may want that condition to persist for only a brief period, to mitigate any body temperature change in reaching the vehicle after leaving the house. Accordingly, the process does not always simply just set the vehicle temperature to match an interior temperature, but instead compares 405 a current home, vehicle and exterior temperature to determine 407 if the vehicle temperature is suitable. A "suitable" vehicle temperature can be defined based on preset conditions for home vs. vehicle and/or exterior comparisons or can be based on observed preferences under certain conditions.

For example, the process may observe that when it is 0 degrees outside and 74 degrees in the home, the user typically sets the heat to "MAX" until the vehicle temperature reaches 80 degrees, and then the user backs the temperature down to 74 degrees a few minutes after the temperature reaches 80. Thus, if the interior temperature is within a threshold variance of 74, if the vehicle interior temperature is below 80 degrees, and if the exterior temperature is within a threshold variance of 0, the process may determine that a suitable vehicle interior temperature is 80 degrees, which should be switched to 74 degrees 3 minutes following user entry.

It is worth noting that the process does not necessarily need to engage heat at MAX if suitable prediction about when a user will use the vehicle can be made, as the point of the user using MAX is to get the heat up as quickly as possible to 80, which the vehicle could achieve more slowly over a longer time if the user was not actually in the vehicle. In such a model, knowledge of vehicle cabin heating rates can be used to determine an appropriate heat setting that will achieve 80 degrees under current conditions prior to a user departure.

In such a manner as above, the vehicle can predict both desirable temperatures under a variety of conditions, and predict change rates that will allow for heating/cooling within a time period without having to use a maximum HVAC setting. This second aspect can aid in saving power and/or fuel while preconditioning the vehicle.

If the vehicle temperature is unsuitable at a current state, given the current home, interior and exterior vehicle conditions, the process may check/use 409 the exterior temperature and determine a rate of temperature change 411 at which the cabin will increase/decrease in temperature, for a given HVAC setting, under current conditions. The process can select an appropriate setting that will heat/cool the vehicle before a user enters, and the process can then engage 413 the HVAC in the manner selected.

If (or when) the vehicle temperature is suitable inside the cabin, the process can determine 415 if the vehicle is moving. In this example, the vehicle process can instruct a home heating/cooling setting, but may wait until the vehicle is moving (the user has actually left the home) before doing so. The process also determines 417 whether another control device (other than, for example, a driver phone) is in communication with a home/office thermostat.

If there is a control device in current communication, the process may forego control instruction for the home system, since this would tend to indicate that a person is present in the home still. Since device communication is used as a proxy for occupant-detection, any other suitable method of home/office occupant-detection could be substituted here. The process may query the home device to determine occupancy (connection of another device, in this instance).

If there is no other control device connected, the process may assume that no one else is home, and the process can again check an exterior temperature 419 and set the home temperature in accordance with the exterior temperature. That is, the user may have different preferred settings based on different exterior temperatures, and the process can adapt and set 421 the home settings based on the user's preferences.

Typical home thermostats, even digital ones, operate under a limited scheduling protocol. That is, they are often fixed to heat or cool, and the settings are typically defined for time periods, but with no accommodation to outside conditions. In areas of high climate change (e.g., deserts, northern states in the late fall and early spring, etc), it is not impossible for the temperature to change 30 or 40 degrees over a given day. By using a reference to an exterior temperature to set an interior setting, the process can switch an interior system between hot and cold and between higher and lower temperatures to more closely accommodate exterior settings. This can result in significant energy usage savings for a user.

For example, a user in the spring may have a system set to cool the house to 68 degrees and to disengage entirely at 11 pm. One morning, after a hot night, the exterior temperature of the house may be 60 degrees and the interior temperature may be 75 degrees (from heat exchange over the hotter night period). Even if the system automatically switched to 72 degrees while the user was away, the process would still cool the house by 3 degrees before switching off. Since the system recognizes that the exterior temperature is actually 68 degrees, the system can instruct the system to forego cooling of the house to 72, since the exterior temperature should help cool the house over the course of the day. The process could periodically communicate with the house thermostat to make sure that rising exterior temperatures are not having a deleterious effect, and could accommodate a desired temperature setting at such a time if needed.

If a vehicle is arriving at a house (e.g., has the house/office as a destination and is within a time or distance threshold), the process may again determine 427 if another control device is already in the home or office. Again, this is a proxy for occupant-detection, and if the other device is present the process may assume that the climate is properly set for that occupant and will exit 429.

If there is no current control device, the process may check a vehicle temperature 431 and exterior temperature 433 and may determine and set 435 a suitable home temperature for when the occupant arrives. As with setting the vehicle temperature, this can be based on predefined comparisons or observed user behavior under various conditions.

Figure 5A:
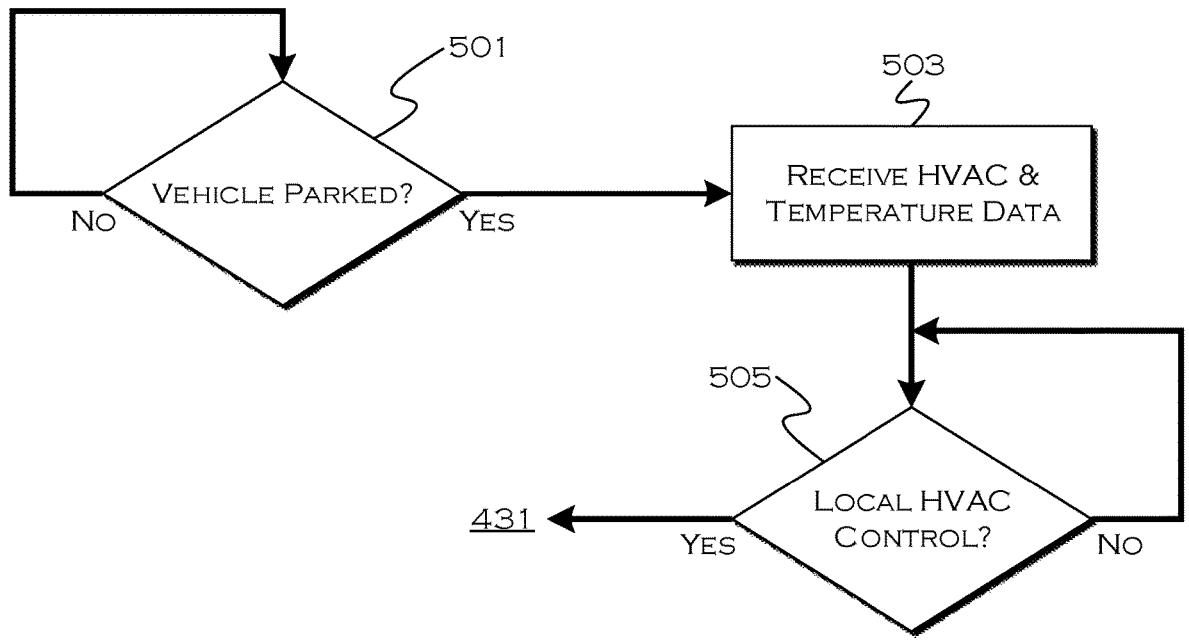
FIGS. 5A and 5B show illustrative examples of portable climate data control processes.
Figure 5B:
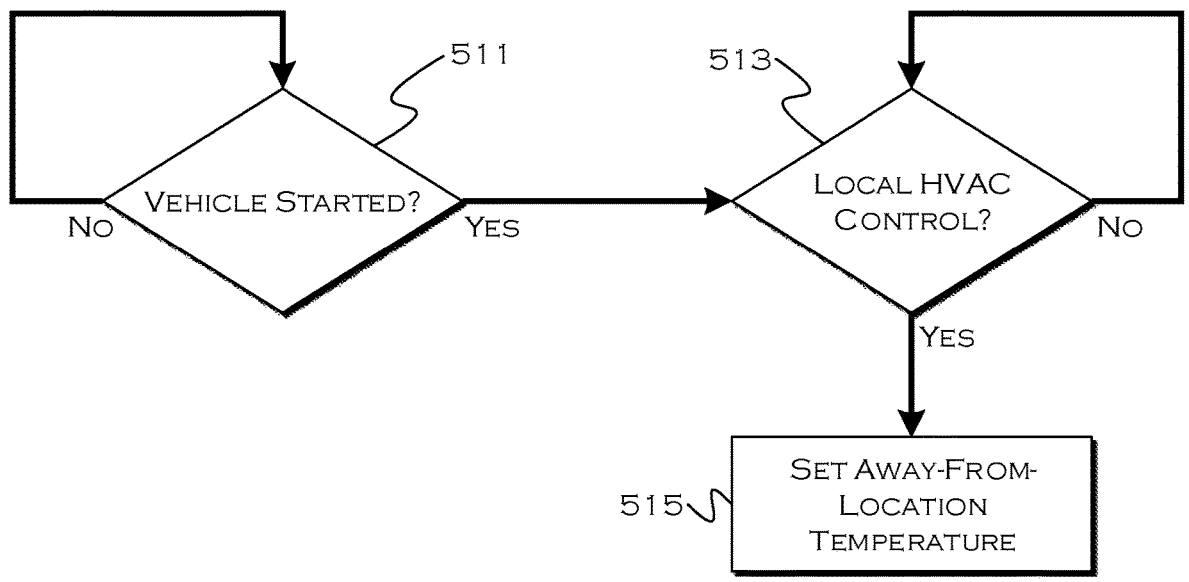

FIGS. 5A and 5B show illustrative examples of portable climate data control processes. This is a fairly simple explanation of how the vehicle settings can control, or be controlled by, a thermostat setting with which the process above cannot directly communicate and/or control. For example, a user's office may have an individual thermostat, which can receive and be controlled by local BLUETOOTH communication, but which cannot or does not otherwise remotely communicate.

In this example, the process determines 501 that a moving vehicle has parked. Once the vehicle is parked, an application executing on a mobile device receives 503 the vehicle HVAC and/or temperature data. This process can determine, as discussed above, what suitable interior settings for a building room would be based on the received data. Once the device is in communicable range 505 of a controllable HVAC system (the exemplary thermostat above), the application can work with the controllable system as described in FIG. 4, step 431, to set and control the system based on the detected vehicle and exterior temperatures.

In the second illustrative process, the device has left an office or other setting as described above. If the device detects a vehicle start 511, the device attempts to determine 513 if a local HVAC control is still in range. In the above system, the HVAC would only still be in range if the vehicle was parked very close to the thermostat, but this would work for many smaller offices. In other systems, the device may need Wi-Fi or cellular access to the thermostat in order to function as next described.

If the device can communicate with the thermostat after the vehicle is started, the device can instruct 515 the local HVAC to be set to an away-from-location setting to save power. In another example, the device works to remotely start the vehicle (precondition the vehicle) and thus is still in short-range communication range of the local HVAC control when the vehicle is actually started (because the device is still in the office).

Figure 6:
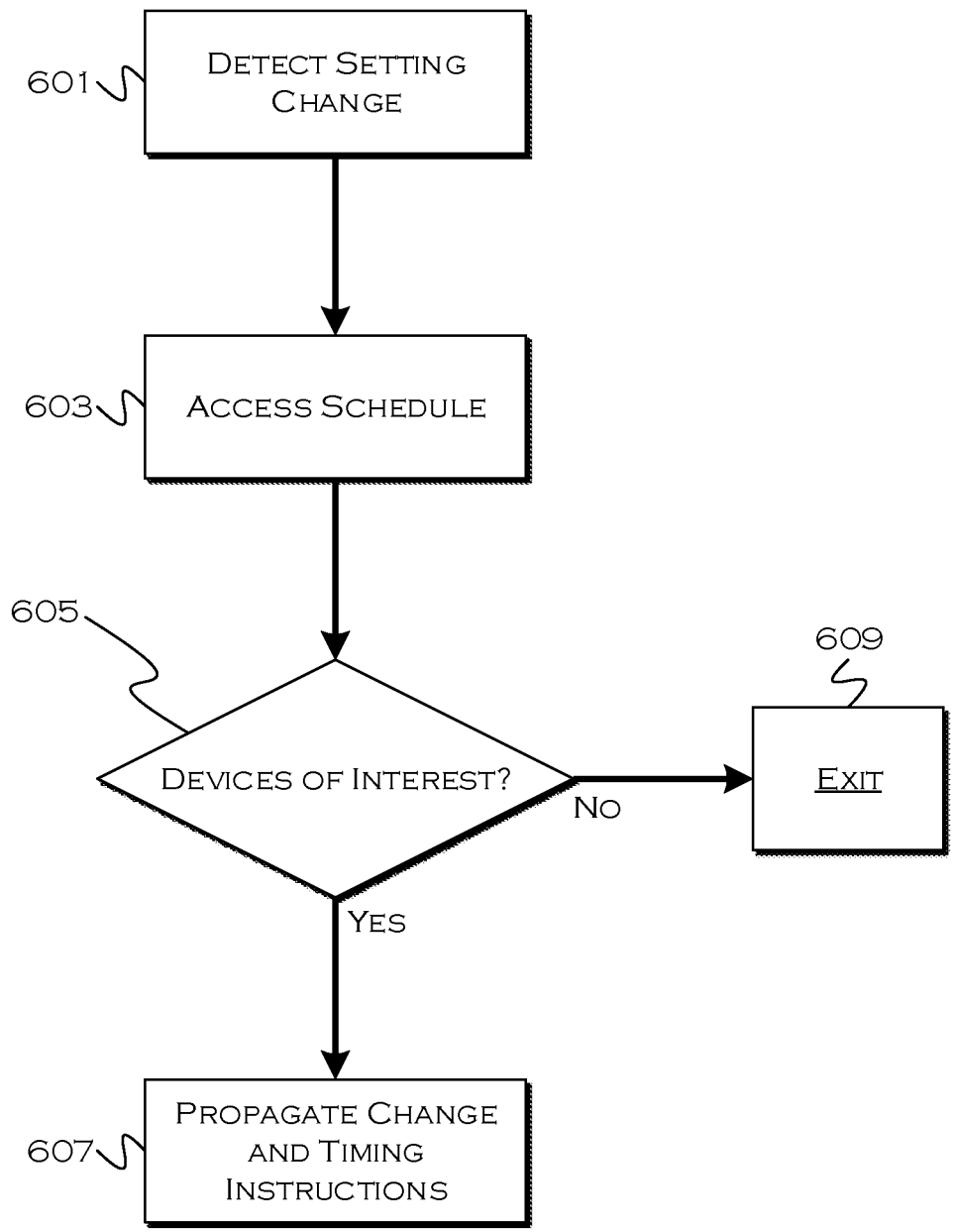
FIG. 6 shows an illustrative example of a climate change propagation process.

FIG. 6 shows an illustrative example of a climate change propagation process. In this illustrative example, a cloud-based system such as that described in FIG. 4 works to unify climate settings across a variety of known and connected environments. For the sake of example, assume that a user has a home, vehicle and office climate control connected to the cloud-system. When one of the climate controls is changed, the process detects 601 the control change, and accesses 603 a known user schedule (user input or predicted) to unify climate settings. If the process determines 605 that the user is likely to encounter any of the other climates controlled by the other climate controls (i.e., identifies controllable devices of interest), the process may propagate 607 the user settings and timing instructions to the various other systems. Otherwise, the process may exit 609.

For example, a user may have a cold and change a home heat setting to 78 degrees. The user may be going to work that day, and the schedule may reflect this. The home setting change may occur at 6 AM, the user may typically leave at 7:15 AM, and the user may arrive at the office around 8 AM. The climate control manager knows the above, and instructs the vehicle to achieve suitable heat (at least 78 degrees, in this case) before 7:15 and the office to achieve suitable heat (again, 78 degrees) before 8 AM. These instructions may rely on local control algorithms or may include explicit instructions as to settings and when to engage the heat.

Using the illustrative embodiments, unification of climate can be achieved across a variety of personal ecosystems with minimal user effort. In a learning model, the user may simply need to provide a few authorizations for communication with the various climate controls, and then based on user behavior the system can "figure out" the appropriate settings. For faster results, the user could set an actual set of preferences based on some or all variables, and the system could directly reference these preferences when setting and determining the various control settings.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined in logical manners to produce situationally suitable variations of embodiments described herein.

What is claimed is:

1. A system comprising:
a processor configured to:
receive a user biometric measurement from a wirelessly connected device;
determine a climate adjustment responsive to a comparison of the biometric measurement to a stored baseline value or range, wherein the baseline indicates a predefined preferred climate control setting at the baseline and wherein a type and degree of the climate adjustment from the predefined setting is based on a type of the biometric measurement, a deviance of the biometric from the baseline and a directionality of the deviance above or below the baseline; and
activate a vehicle climate control to reflect the climate adjustment.

2. The system of claim 1, wherein the wirelessly connected device performs the biometric measurement.

3. The system of claim 1, wherein the wirelessly connected device receives the biometric measurement from a separate biometric measuring device.

4. The system of claim 1, wherein the type of biometric measurement includes heart-rate.

5. The system of claim 4, wherein the climate adjustment includes changing a vehicle temperature responsive to a heart-rate outside the stored value or range, wherein the type of change includes raising the temperature when. the heart-rate is low and lowering the temperature when the heart rate is high, and wherein the degree of raising or lowering is determined based on a magnitude of the deviance from the baseline.

6. The system of claim 1, wherein the type of biometric measurement includes skin temperature.

7. The system of claim 6, wherein the type of climate adjustment includes lowering a vehicle temperature responsive to a skin temperature above the stored value or range.

8. The system of claim 6, wherein the type of climate adjustment includes raising a vehicle temperature responsive to a skin temperature below the stored value or range.

9. The system of claim 1, wherein the climate adjustment includes varying a vehicle temperature, and wherein the processor is configured to activate the vehicle climate control at a level and for a duration expected to achieve the climate adjustment before a user is expected to enter the vehicle, based on an expected user entry time.

10. A system comprising:
a processor configured to:
determine that a first user will transition from a first climate-controllable environment to a second climate-controllable environment within a threshold time;
detect whether a second-user control device is in communication with a second-environment climate control for the second climate-controllable environment, responsive to a difference resulting from comparing first and second environment temperatures; and
set the second-environment climate control to a desired temperature, based on the first environment temperature, responsive to an absence of the second-user control device.

11. The system of claim 10, wherein the processor is configured to determine the desired temperature based on observed user preferences previously stored, corresponding to a preferred second environment emperature based on the first environment temperature and an outside temperature.

12. The system of claim 10, wherein the first environment is a vehicle and the second environment is a building.

13. The system of claim 12, wherein the processor is configured to determine that the user will transition to the second environment based on an expected vehicle arrival time.

14. The system of claim 10, wherein the first environment is a building and the second environment is a vehicle.

15. The system of claim 14, wherein the processor is configured to determine that the user will transition to the second environment based on a stored user schedule.

16. The system of claim 14, wherein the processor is further configured to:
detect whether the second-user control device is in communication with a first-environment climate control; and
set the first-environment climate control to a desired temperature, based on a user-defined away-temperature, responsive to an absence of the second-user control device and a determination that the first user has departed the first environment.

17. The system of claim 16, wherein the determination that the user has departed is based on determining that the vehicle has moved away from the building.

18. The system of claim 10, wherein the processor is further configured to:
determine a temperature change rate for the second environment, based on the second environment temperature and an outside temperature; and
instruct the second-environment climate control to engage such that the second environment reaches the desired temperature, based on the change rate, before a determined user transition time.

19. A system comprising:
a processor configured to:
detect a user-initiated change to a current environment control;
determine if another environmental control is predefinedly associated with a user enacting the user-initiated change:
determine when a user will likely transitiontraaisition to another environment controlled by the another environmental control; and
instruct the another environmental control to adjust a temperature to reflect the user-initiated change, at a time within a predetermined threshold before the user will likely transition, wherein the predetermined threshold is no less than. an expected amount of time for the another environment to adjust to reflect the temperature, the amount of time determined by the processor based on a rate of temperature change based on current another environment temperature, current outside temperature, and previously observed temperature change rates under same conditions.

* * * * *